Figure 1:
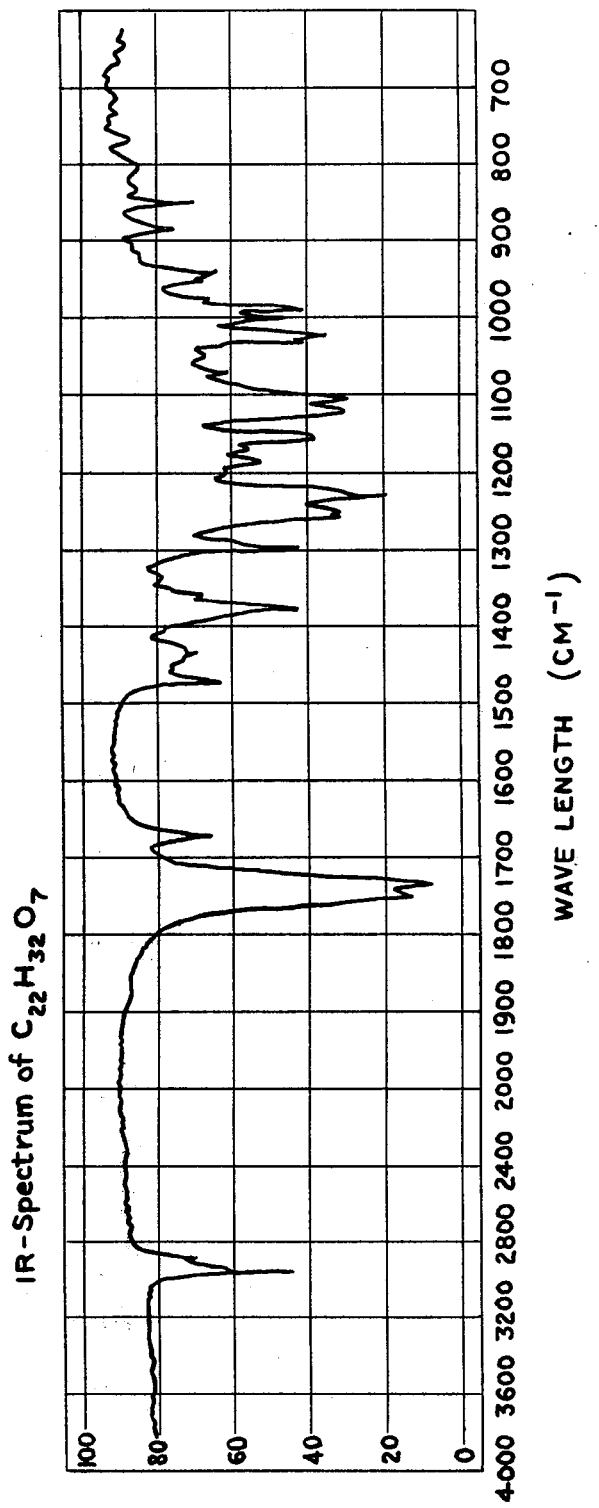

United States Patent [19]

Thies

[11] 4,205,083

[45] May 27, 1980

[54] CYCLOPENTAPYRANS

[75] Inventor: Peter W. Thies, Hanover, Fed. Rep. of Germany

[73] Assignee: Kali-Chemie AG, Hanover, Fed. Rep. of Germany

[21] Appl. No.: 869,385

[22] Filed: Jan. 13, 1978

Related U.S. Application Data

[63] Continuation-in-part of Ser. No. 519,986, Jan. 11, 1966, abandoned, and a continuation of Ser. No. 601,548, Apr. 8, 1975, abandoned, which is a continuation of Ser. No. 401,904, Sep. 28, 1973, abandoned, and Ser. No. 764,199, Oct. 1, 1968, abandoned, which is a continuation-in-part of Ser. No. 519,986.

[30] Foreign Application Priority Data

Mar. 30, 1968 [DE] Fed. Rep. of Germany ....... 1768092

[51] Int. Cl.$^2$ ..................... A61K 31/33; C07D 407/02
[52] U.S. Cl. .................................. 424/283; 260/345.2
[58] Field of Search ...................... 260/345.2; 424/283

[56] References Cited

U.S. PATENT DOCUMENTS

| | | | |
|---|---|---|---|
| 3,422,090 | 1/1969 | Thies et al. | 260/345.2 |
| 3,428,652 | 2/1969 | Sigg et al. | 260/345.2 |
| 3,585,215 | 6/1971 | Thies | 260/345.2 |
| 3,869,476 | 3/1975 | Thies et al. | 260/345.2 |

OTHER PUBLICATIONS

Thies, Tetrahedron, vol. 24, pp. 313 to 347 (Jan. 1968).
Thies, Tetrahedron Letters, No. 11, pp. 1163-1170 (1966).

*Primary Examiner*—John D. Randolph
*Attorney, Agent, or Firm*—Schwartz, Jeffery, Schwaab, Mack, Blumenthal & Koch

[57] ABSTRACT

Novel cyclopentapyran esters are produced from specific plants of the genus Valeriana, i.e. from *Valeriana mexicana* or *Valeriana toluccana*. Said esters have a high tranquilizing and sedative effect which is superior to that of known cyclopentapyran esters produced from Valeriana officinales and the like Valeriana species.

7 Claims, 5 Drawing Figures

NMR-Spectrum of $C_{22}H_{32}O_7$

NMR-Spectrum of $C_{23}H_{34}O_8$

NMR-Spectrum of $C_{22}H_{32}O_8$

CYCLOPENTAPYRANS

The present application is a continuation-in-part of application Ser. No. 519,986 entitled "NEW THERAPEUTICALLY ACTIVE COMPOUNDS" and filed Jan. 11, 1966; and a continuation of application Ser. No. 601,548, filed Apr. 8, 1975 and entitled "NEW CYCLOPENTAPYRANS", which application in turn is a continuation of application Ser. No. 401,904, filed Sept. 28, 1973 and of application Ser. No. 764,199, filed Oct. 1, 1968, which in turn is a continuation-in-part of application Ser. No. 519,986, entitled "NEW THERAPEUTICALLY ACTIVE COMPOUNDS" and filed Jan. 11, 1966, said applications Ser. No. 601,548, Ser. No. 401,904, Ser. No. 764,199, and Ser. No. 519,986 being abandoned.

This invention relates to novel esters of epoxy cyclopentapyrans which can be represented by formula

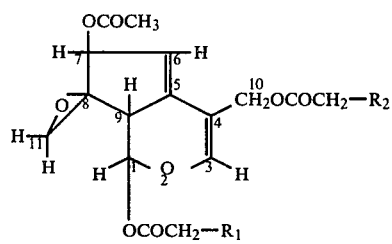

hereinafter referred to as compounds I, in which $R_1$ and $R_2$ represent each one an isopropyl or an isobutyl group, and the corresponding 5,6-dihydro saturated esters referred to as compounds II in which $R_1$ and $R_2$ have the same definition as above.

The invention also relates to novel esters of unsaturated cyclopentapyrans, which can be represented by the formula

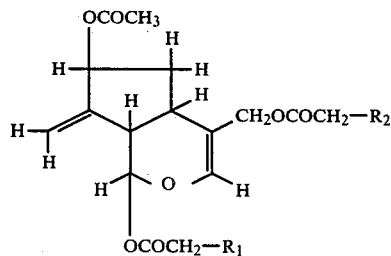

herein referred to as compounds III, in which $R_1$ and $R_2$ represent each an isopropyl or an isobutyl group.

Such cyclopentapyran esters have been broadly designated as Valepotriates for purpose of convenient and generic reference.

The novel esters of the invention are valuable therapeutics, particularly remarkable tranquilizers free of hypnotic effects useful in human therapy. The esters also possess analgesic properties and bacteriostatic effects especially against bacteria of the type Mycobacterium.

The class of esters represented by Formula I and II are obtained by extraction of comminuted roots and rhizomes of specific plants of the family Valerianaceae at a low temperature, preferably not above 30° C. with a lipophilic solvent in the presence of an aliphatic carboxylic acid, preferably having 2 to 7 carbon atoms, in a mildly acidic pH range preferably from about 3 to about 7. Desirably, the extraction is carried out in the presence of a suitable buffering agent, preferably an alkali metal salt or ammonium salt of an aliphatic carboxylic acid. Extraction of the undesired accompanying substances from the concentrated crude extract is carried out by extracting with benzine or higher hydrocarbon, the acid solution of the crude extract, for instance in a concentrated carboxylic acid such as acetic acid, or in its alcoholic solution. After discarding the organic extract, the acid solution is diluted with water and the acid aqueous phase is extracted with a lipophilic solvent, such as benzine, an equivalent hydrocarbon or a halogenated hydrocarbon. The combined extracts are neutralized, dried, and clarified to yield a mixture of both the saturated and unsaturated esters of Formulas I and II, respectively.

The separation of the esters is carried out by subjecting the extract in a hydrophobic solvent to chromatographic adsorption on alumina partly inactivated by treatment with a carboxylic acid, preferably of 2 to 7 carbon atoms, under non-aqueous conditions.

The specific group of Valerianaceae from which esters I and II are obtained by the above method is *Valeriana mexicana* or *Valeriana toluccana* D.C.

The specific group of Valerianaceae from which esters II in which $R_1=R_2=$isopropyl or isobutyl and esters III are obtained by the above method is further described below.

The usual aqueous or alcoholic extracts of Valerian according to the Pharmacopeias do not contain the esters of the invention. These are either water-insoluble or resinify soon upon standing in alcoholic solutions. The commercial alcoholic Valerian tinctures also do not contain such esters but rather artefacts, as is evident from the dark coloring of the Valerian tincture.

It has been found that the esters of the invention are obtainable from a very specific group of roots and/or rhizomes of plants of the genus Valeriana. Within the various botanical types of the genus Valeriana and genus Centranthus, there has been found to exist certain types which are chemically differentiable particularly with respect to their property to yield a high amount of individual cyclopentapyrans. Yet these plants which are differentiable on the basis of the chemical compounds derivable therefrom are not distinguishable with reference to botanical criteria. The property to accumulate specific cyclopentapyrans is inherited genetically, as has been demonstrated by years of botanical and chemical control of generations of offsprings of selected parent strains of such plants.

It has now been found that certain Valeriana types, natives of Mexico and Guatemala, designated as *Valeriana mexicana* and *Valeriana toluccana* D.C. are excellent sources of the esters I and II of the invention. They yield up to about 5% of the ester $C_{22}H_{30}O_8$ of Formula I, and 2% of the corresponding 5,6-dihydro ester $C_{22}H_{32}O_8$. In contrast, the yield of these esters from Valeriana officinalis is negligible and is consistently less than 0.05%.

After extensive research it was furthermore discovered that the heretofore unknown type of *Valeriana wallichii* D.C. originating from the specific geographic area of the forested Himalayas lying west of the river Indus is ideally suited to yield the 5,6-dihydro ester $C_{22}H_{32}O_8$ in which $R_1=R_2=$isopropyl and the homologous isocaproic acid esters $C_{22}H_{32}O_8$ of this invention when treated in accordance with the process hereinafter described. In contrast, *Valeriana wallichii* originating from the remainder of the Himalayas extending Eastward of the Indus to China and southeast in Pakistan beyond India, Nepal and Tibet to Bhutan does not yield the esters of the invention in any significant amounts.

The new esters of the invention are remarkable therapeutic agents which exhibit a unique heretofore unknown equilibrium or balanced effect on the psyche and the organism of humans. This balanced effect is clearly distinguishable from the effect of heretofore known sedatives in that the tranquilizing effect of the esters of the invention is free of the feeling of tiredness, or drowsiness traditionally associated with such sedatives, but rather increases the ability to perform efficiently, hence the use of the term "balanced effect". In contrast to known sedatives and tranquilizers, the esters of the invention do not impair the driving capability and do not increase the effects of alcohol and of hypnotics. Several years of research in pediatrics and geriatrics confirm that the esters of the invention are useful in the therapy of psychiatric cases and nervous conditions, difficulties in adaptability and lack of motivation of the aged as well as of nervous disturbances in the development of children, like poor eating, poor school performance and difficulties in relating to others, lack of concentration ability and lack of contact with reality.

The balanced tranquilizing effect discussed above was also demonstrated on mice, rats and cats in standard labyrinth, rotating rod and wheel tests.

Excellent results were also obtained in alcoholic withdrawal cures in which curing of the patients heretofore never observed was demonstrated.

Additional pharmacological evaluation of the esters of the invention is carried out in accordance with standard well-recognized tests.

The esters of the invention are tested individually and in mixture thereof.

Acute Toxicity

Acute toxicity $LD_{50}$ is determined on albino mice (Type NMR 1) weighing 18 to 20 g and on albino rats weighing 140 to 180 g. Amounts used are mg/kg; parts are by weight. The $LD_{50}$ of the following compounds on the mouse amounted to

TABLE I

| Compound | Intra-peri-tonal | oral |
|---|---|---|
| Compound I with $R_1 = R_2$ = isopropyl ($C_{22}H_{30}O_8$) | 75 | >3,200 |
| Compound II with $R_1 = R_2$ = isopropyl ($C_{22}H_{32}O_8$) | 1,250 | >1,470 |
| Mixture consisting of 60 parts of compound II with $R_1 = R_2$ = isopropyl ($C_{22}H_{32}O_8$) 20 parts of compound II with $R_1$ = isobutyl and $R_2$ =isopropyl ($C_{23}H_{34}O_8$) 5 parts of compound III with $R_1$ = $R_2$ = isopropyl ($C_{22}H_{32}O_7$) 5 parts of compound III with $R_1$ = isobutyl $R_2$ = isopropyl ($C_{23}H_{34}O_7$) 10 parts of compound I with $R_1$ = $R_2$ = isopropyl ($C_{22}H_{36}O_8$) | :67 | 1,470 |

Chronic Toxicity

Daily oral administration of doses of 60 mg/kg of the above mixture of compounds to dogs (English beagles) for twenty-six weeks showed no organic effect except a brownish coloring of the tongue and of the renal cortex. The results of hematological, biochemical and urine analysis showed normal values.

The esters of the invention also possess analgesic properties. In standard analgesic tests (Writhing-test) oral administration of doses of 562 mg of ester II with $R^1=R^2=$isopropyl and 1000 mg of ester I with $R^1=R^2=$isopropyl per kg was equally effective as 42 mg of amidopyrin per kg p.o.

The analgesic effect is a useful therapeutic property in addition to the above-described unique tranquilizing properties of the esters.

The esters also possess unexpectedly bacteriostatic properties. Standard testing methods were used. The results are given in limit dosages which have a 100% bactericidal effect.

TABLE II

| BACTERIOSTATIC PROPERTIES | | |
|---|---|---|
| Microorganisms | Compound I with $R^1 = R^2$ = isopropyl | Compound II with $R^1 = R^2$ = ispropyl |
| Staphylococcus p. aureus (Micrococcus) | 0.5 mg/ml | 5.0 mg/ml |
| Staphylococcus S. G. 511 (Micrococcus) | " | " |
| Bacterium coli 126 (Escherichia) | 5.0 mg/ml | " |
| Bacterium proteus (Proteus vulgaris) | " | " |
| Bacterium pyocyaneum | " | " |
| Mycobacterium phlei | 0.1 mg/ml | 0.1 mg/ml |
| Mycobacterium smegmatis | " | " |
| Mycobacterium lacticola | " | " |

Upon consideration of the data it is noteworthy that while the bactericidal effect of the esters is moderate on common bacteria associated with unsanitary conditions, the esters are highly effective in the control of bacteria of the genus mycobacterium (at least 50 times more effective). Particularly in view of the esters' low toxicity, this effect suggests their use in the control of tuberculosis.

It is evident from the above data that the esters of the invention possess a combination of unique and valuable properties.

In therapy with the esters of the invention, individual dosages of 50 mg are especially useful. In psychiatric clinics daily dosages up to 600 mg were administered for several days without side effects with good therapeutic result.

The following non-limiting examples illustrate the invention.

EXAMPLE 1

Preparation of $C_{22}H_{30}O_8$ and 5,6-dihydro $C_{22}H_{32}O_8$ esters of Formula I from *Valeriana mexicana* D.C.

30 kg ground roots and rhizomes of *Valeriana mexicana* are stirred into a paste in a 60 l. percolator with 45 l. of acetic acid ester containing 1% of glacial acetic acid. After allowing the mixture to stand for 24 hours at room temperature, the percolation is carried out in such a way that within two days, with portionwise addition of another 45 l. a percolate of a total of 60 l. is obtained.

An additional 20 liters to wash the column are then percolated through. The total yield of 80 l. of percolate is washed with water, dried over sodium sulfate ($Na_2SO_4$) and concentrated in a rotary evaporator at 30° C. The product is a highly viscous, dark brown, crude ester extract of 2.9 kg=yield 9.67%, with respect to the starting plant material.

The separation of the esters from undesirable etherified oils, undetermined fatty acid esters and other undesirable compounds is performed by dissolving 1 kg of the crude ester extract in 10 l. of 90% acetic acid at 10° C. The solution is extracted three times with 3 l. of benzene saturated with 90% acetic acid; the benzine phase is discarded.

The acetic acid phase is then diluted step-wise with water to a volume of 1.5 times that of the extract and then extracted 6 times with 6 l. of benzene each. The benzene extracts are combined and are then neutralized by washing twice with 10 l. each of water and once with 10 l. of 0.25% sodium hydroxide; then the extract is dried over sodium sulfate, clarified with charcoal and concentrated in a vacuum at 30° C. to constant weight.

The total yield of purified epoxy esters was 0.474 kg of a yellow oil kg=4.6%, with respect to the dried original starting material.

EXAMPLE 2

Separation and purification of the ester $C_{22}H_{30}O_8$ from the corresponding 5,6-dihydro ester.

5 kg of aluminum oxide (Woelm, activity state I according to Brockmann) were inactivated by suspending in a mixture of 500 ml of ethyl methyl ketone, 750 ml of glycerol monoacetate, 100 ml of propionic acid, 50 ml of acetic acid and 3 l. of n-hexane. After cooling to room temperature (to dissipate the heat generated by the reaction of the aluminum oxide with the solvent mixture), the suspension is introduced into a column (provided with a cooling jacket) and the aluminum oxide is washed with 15 l. of hexane until free of the ketone. The alumina column is now ready for treatment of the extract.

250 g of the purified extract dissolved in 150 ml of hexane were introduced into the column. The elution speed amounted to 10 ml/min.; the temperature 15° C. A total of 25 l. of hexane are used for elution. 42 fractions of 0.5 l. were collected. The epoxy cyclopentapyran ester $C_{22}H_{30}O_8$ I is found in eluate fractions 6 to 26. The control of the collected eluate fractions was effected by thin-layer chromatography.

All fractions containing the epoxy cyclopentapyran $C_{22}H_{30}O_8$ were combined to yield about 10 l., and were concentrated to 2 l., washed free of acid by means of 0.2 l. of a 1% sodium bicarbonate solution and 2 l. of water, dried over sodium sulfate, decolorized with charcoal, and concentrated in a vacuum.

The pure epoxy cyclopentapyran of Formula I in which $R_1$ and $R_2$ are both isopropyl is obtained in a yield of 96.3 g=38.52% based on the concentrated starting oil.

The ester is a colorless highly viscous oil of aromatic odor and a somewhat soapy, bitter and burning taste.

It has the following characteristics:
empirical formula: $C_{22}H_{30}O_8$
$n_D^{20}=1.4923$; $\alpha_D^{22}=+154°$ (in methanol)

The further differentiation of the epoxy cyclopentapyran ester is carried out by running an IR- NMR- and UV-spectrum of the ester but this is found not to be determinative because of the similarity with the isomer ester $C_{22}H_{30}O_8$, described in U.S. Pat. No. 3,869,476.

To further confirm that the ester according to the present invention has an isovaleroxymethyl substituent in the 4-position of the pyran ring, said ester is heated to 100° C. and the thermal degradation product is identified by thin-layer chromatography to be identical with homobaldrinal, $C_{15}H_{16}O_4$, that is, 4-isovaleroxymethyl-7-formylcyclopenta(c)pyran. In comparison, thermal degradation of the epoxy cyclopentapyran having an acetoxymethyl group in the 4-position of the pyran gives, upon identical thermal degradation the known compound baldrinal, $C_{12}H_{10}O_4$, that is, 4-acetoxymethyl-7-formyl-cyclopenta-(c)pyran.

Figure 4:
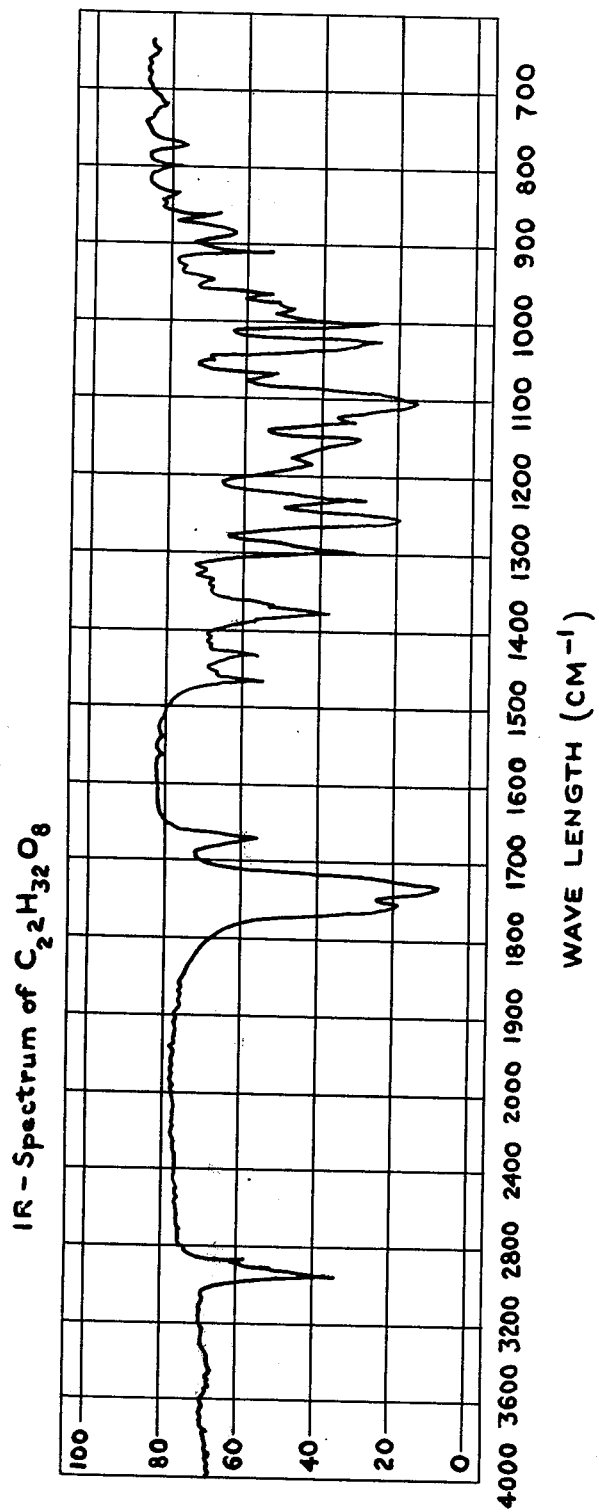
Figure 5:
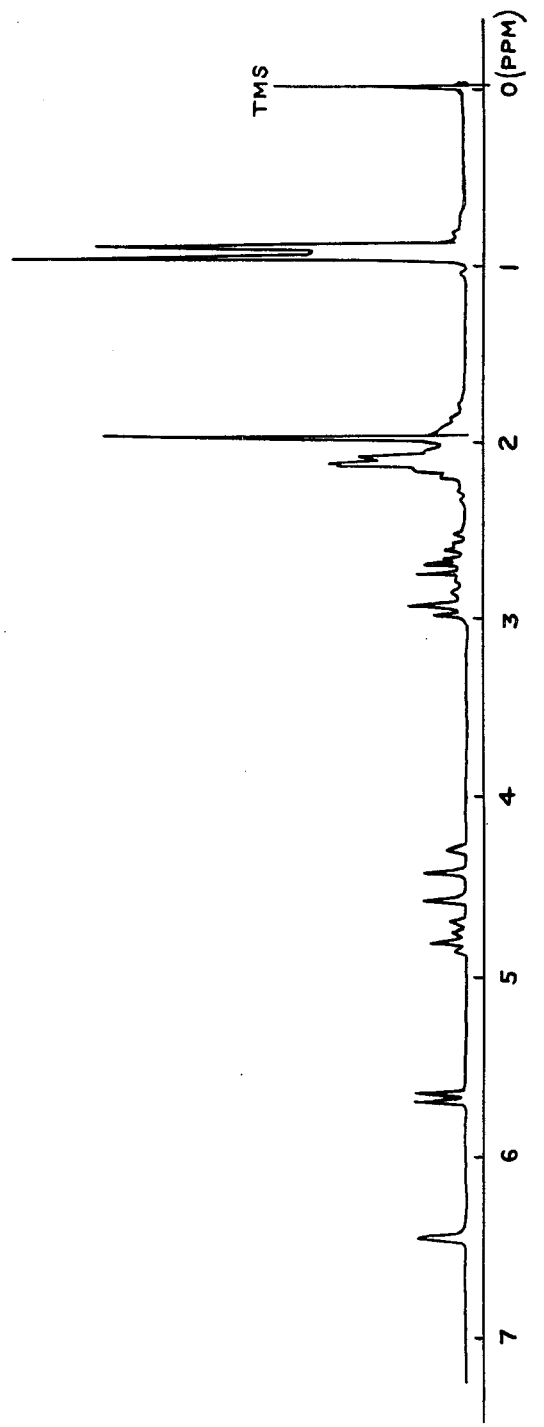

Upon continuing the elution of the extract with hexane there are obtained from fractions 27 to 34, 56.1 g of a crystallizing mixture of the ester $C_{22}H_{30}O_8$ of Formula I ($R_1$ and $R_2$=isopropyl) and of the corresponding 5,6-dihydro compound $C_{22}H_{32}O_8$. Upon recrystallization from a mixture of petroleum ether/ether there is obtained a yield of 10.8% of pure ester based on the starting oil. 27 g of 5,6-dihydro epoxycyclopentapyran in which $R_1$ and $R_2$=isopropyl are obtained. The product has the following characteristics:
m.p. 63°–64° C. (Kofler).
$\alpha_D^{22}=-79°$ (in methanol).
IR- and NMR-spectrum are shown in FIG. 4 and FIG. 5 respectively.

EXAMPLE 3

Preparation of 5,6-dihydro epoxycyclopentapyran with $R_1=R_2$=isopropyl ($C_{22}H_{32}O_8$) from *Valeriana wallichii* D.C. from the Himalaya forests west of the Indus.

Rhizomes of *Valeriana walichii* D.C. obtained from the forested areas of the Himalaya west of the Indus were treated as follows: 60 kg are ground into a paste as in Example 1 with acetic acid ester containing 1% of acetic acid, and percolated. The percolate is then washed free of acid with sodium hydroxide solution, dried over sodium sulfate, clarified with charcoal, then concentrated in a vacuum at 30° C. to constant weight. The yield is 4.602 kg=7.7%, of a crude light brownish oil.

This crude oil is separated from the undesired accompanying products following the procedure of Example 1, by dissolving the oil in 90% glacial acetic acid and then shaking with benzene saturated with 90% acetic acid. The benzene phase is discarded. The acetic acid phase is extracted with benzene after dilution with water and the benzene extract is washed free of acid with a sodium hydroxide solution, dried over sodium sulfate, clarified with charcoal and concentrated in a rotary evaporator at a temperature of about 30° C. to constant weight. The yield is 1.463 kg of the purified oil=2.44%, with respect to the dried rhizome.

This oil crystallizes on standing several days at 5° C. After recrystallization from a mixture of ether/hexane (1:9) there is obtained 0.952 kg of white needles of pure 5,6-dihydro epoxycyclopentapyran ($C_{22}H_{32}O_8$)=1.58% based on the dried rhizome and 65.0% based on the purified ester oil.

The physical and other analytical data as well as the IR- and NMR-spectra conforms with those of Example 1 of the 5,6-dihydro epoxycyclopentapyran ester of Formula II ($C_{22}H_{32}O_8$).

It is evident that the ester can be obtained from this plant source without column chromatography in amounts generally of 2.8%.

EXAMPLE 4

Preparation of the esters of Formulas II and I.
5 kg of aluminum oxide (Woelm) are treated similarly as in Example 1 with a mixture of 500 ml of ethyl methyl ketone, 750 ml of glycerol monoacetate, 100 ml of propionic acid, 50 ml of acetic acid and 2000 ml of n-heptane to partially deactivate the column. 50 l. of n-heptane are used to wash the column once more.

44 g of the partially crystallized mother liquor of 5,6-dihydro epoxycyclopentapyran $C_{22}H_{80}O_8$ obtained from Example 3 are dissolved in 250 ml of n-heptane and 50 ml of acetic acid ethyl ester and then introduced on the partially deactivated column. After penetration of the solution, the elution was started with n-heptane. The dropping rate was about 5 ml/min.; the size of the fractions 100 to 500 ml. The control of the individual fractions was effected by thin-layer chromatography.

Fractions 1 to 9 are washed with 0.5% potassium carbonate solution and water until neutral, concentrated under vacuum to yield 0.44 g. Upon crystallization from ether/petroleum ether (1:2) there are obtained 0.136 g of a mixture of the esters $C_{22}H_{32}O_7$ and $C_{23}H_{34}O_7$ which crystallized as white needles of m.p. 53°-60° C.

The isolation of $C_{22}H_{32}O_7$, the ester of Formula II in which $R_1=R_2=$isopropyl, proceeds as follows: The mixture of esters described above is recrystallized twice from a mixture of ethanol/water whereupon there are obtained about 20 mg of esters $C_{22}H_{32}O_7$ which has the following characteristics: m.p.—68°-70° C.

Molecular weight: 408.5.

Calculated: 64.68% C, 7.90% H calc., 27.42% O calc; Found: 64.33% C, 8.13% H, 27.54% O.

UV-spectrum: $\lambda max \approx 204$ m$\mu$(in methanol).

Figure 2:
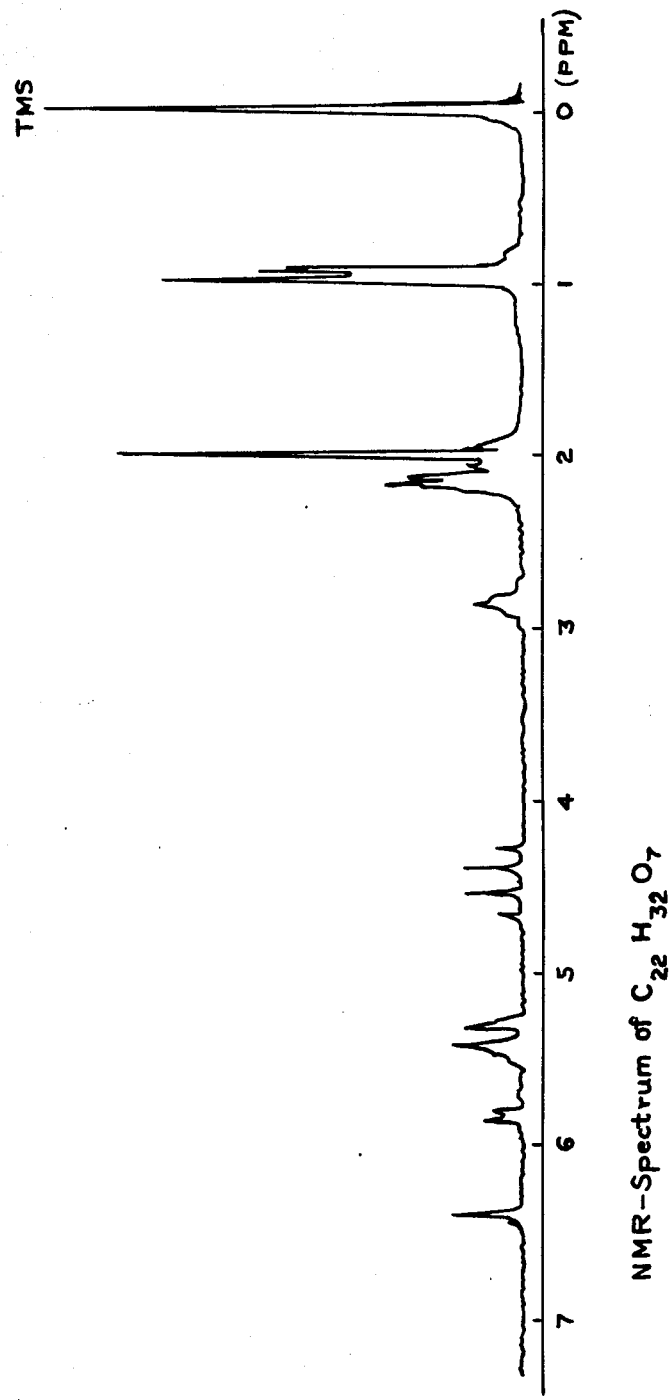

IR-spectrum and NMR-spectrum: are shown in FIGS. 1 and 2, respectively.

Isolation of $C_{23}H_{34}O_8$ (Formula I) in which $R_1=$isobutyl and $R_{2'=isopropyl}$ 5,6-dihydro epoxycyclopentapyran.

The elution is continued with n-heptane collecting fractions 40-60 which are then concentrated under vacuum to yield 7.527 g of a crystallizing product. The product is recrystallized several times from a mixture of petroleum ether/n-heptane/ether (25:25:5). There are obtained 1.46 g of the ester $C_{23}H_{34}O_8$. The ester has a constant m.p. of 50°-51° C.

Molecular weight: 438.52.

Calculated: 63.00% C, 7.82% H, 29.18% O; Found: 63.14% C, 7.84% H, 29.2% O.

$a_d^{21}=-72°$ (in methanol).

UV-spectrum: $\lambda$ max$\approx$206 m$\mu(\epsilon=6400)$ in methanol.

Figure 3:
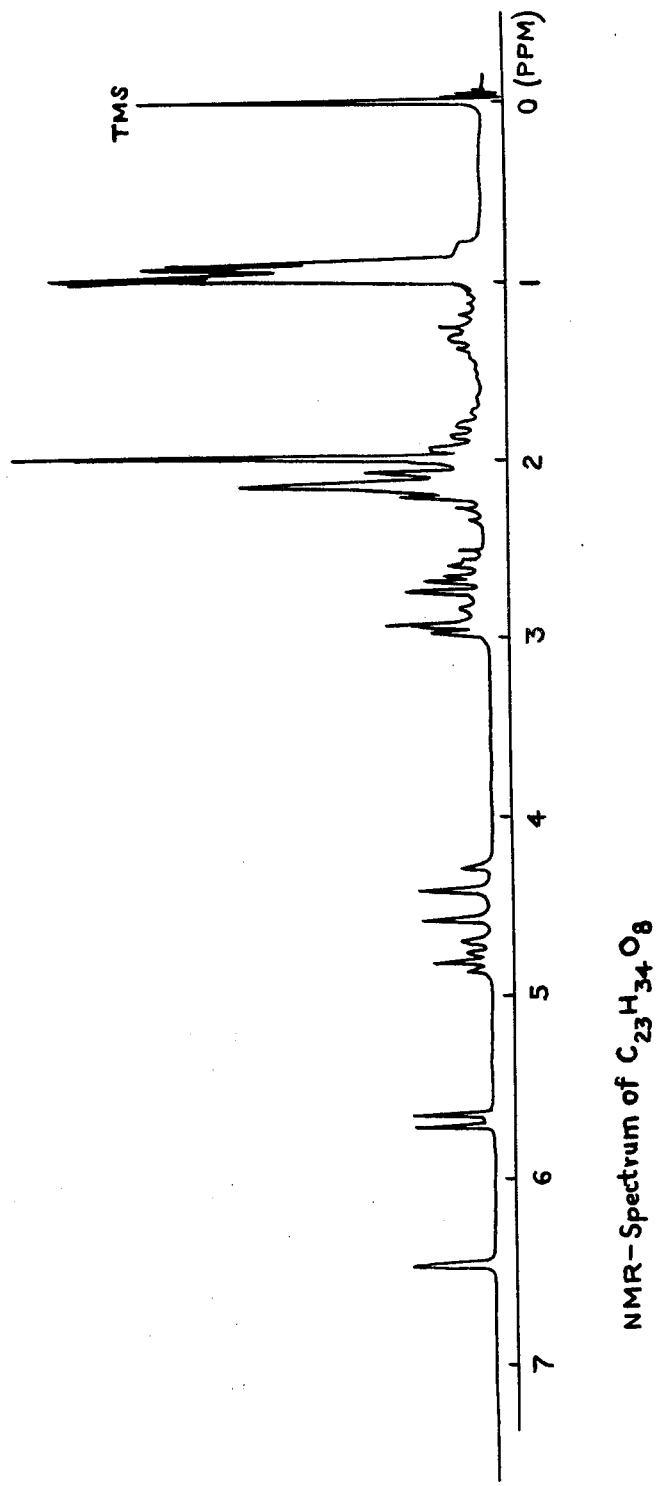

NMR-spectrum: is shown in FIG. 3.

The elution is continued and fractions 61-84 yield a total of 12.61 g of mixed crystals of the esters $C_{23}H_{34}O_8$ and $C_{22}H_{32}O_8$ having a m.p. of 54°-56° C. This is a mixture of the dihydro ester of Formula I in which $R_1=$isobutyl and $R_2=$isopropyl and of the ester of Formula I in which $R_1$ and $R_2$ are isobutyl.

From fractions 85-91 there is obtained 18.4 of pure 5,6-dihydro epoxycyclopentapyran $C_{22}H_{32}O_8$.

Lipophilic solvents which are especially suitable for the extraction process include, in addition to those described above, hydrocarbons, halogenated hydrocarbons, ethers, esters, ketones or alcohols. The carboxylic acids are preferably monocarboxylic acids having 2-7 carbon atoms, more preferably acetic acid, or their acid derivatives, if desired, together with their alkali metal or ammonium salts. The extraction can also be carried out with the carboxylic acids alone without lipophilic solvents, preferably in admixture with their salts which act as buffers. Supplementary details of the process are found in U.S. Pat. No. 3,869,476.

The 5,6-dihydro saturated esters are obtainable by known mild hydrogenation methods of the corresponding epoxy-5,6-unsaturated esters.

Likewise, by known chemical methods of transesterification the $R_1$ and $R_2$ radicals are readily substitutable and interchangeable so that from the ester in which $R_1$ and $R_2$ are isopropyl the corresponding mixed isopropyl isobutyl ester or the diisobutyl ester can readily by prepared.

The same applies for the esters of Formula II.

I claim:

1. A cyclopentapyran ester $C_{22}H_{30}O_8$ of the formula

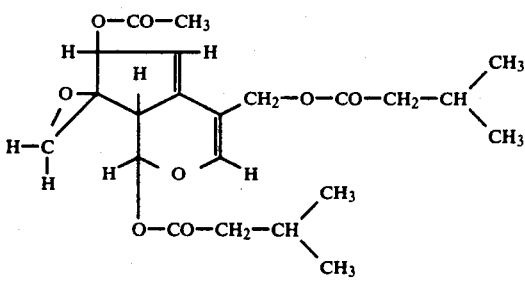

said ester, in the substantially pure state, having a refraction index $n_D^{20}=1.4923$ and an optical rotation of $[\alpha]_D^{21}=+151°$ (in methanol), said ester, on degradation by heating to 100° C. and chromatographical separation, yielding 4-isovaleroxy methyl-7-formyl cyclopenta(c)pyran as thermal degradation product.

2. In a process of producing the cyclopentapyran ester of the formula

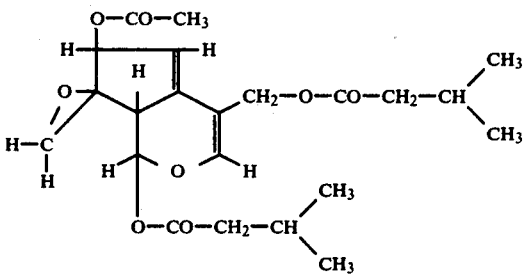

said process comprising the steps of extracting comminuted roots or rhizoma of plants of the genus Valeriana with a lipophilic solvent having added thereto an aliphatic carboxylic acid having 2 to 7 carbon atoms in its molecule at a slightly acidic pH range, concentrating the resulting extract, dissolving the concentrated extract in concentrated acetic acid, treating the resulting acid solution with a lipophilic solvent, discarding the lipophilic solvent solution, diluting the acetic acid phase with water, and extracting the cyclopentapyran esters from said diluted aqueous acid solution with a water-insoluble organic solvent, the improvement which consists in subjecting the roots or rhizomas of the Valeriana plants of the species *Valeriana mexicana* or *Valeriana toluccana* D.C. to said extraction and purification process.

3. The process of claim 2, in which the resulting extract in the water-insoluble organic solvent is subjected to chromatographic adsorption on an aluminum oxide adsorbent, said aluminum oxide adsorbent being partly inactivated by a treatment with an aliphatic carboxylic acid having 2 to 7 carbon atoms in a water-free medium, wherefrom the cyclopentapyran ester of the formula given in Claim 2 is fractionally eluted.

4. The process of claim 3, in which the eluting agent is a lipophilic solvent.

5. The process of claim 4, in which the lipophilic solvent is hexane.

6. In a method of producing a balanced tranquilizing and sedative effect without causing drowsiness in humans or animals, the step which comprises administering to humans or animals an effective amount of the compound of claim 1.

7. In a method of treating humans or animals affected by bacterial infections and especially by infections caused by bacteria of the Mycobacterium group, the step which comprises administering to such humans or animals an effective amount of the compound of claim 1.

* * * * *